(12) United States Patent
Qureshi et al.

(10) Patent No.: US 11,717,395 B2
(45) Date of Patent: Aug. 8, 2023

(54) INTRA-OCULAR LENS FOR EXTENDED MACULAR VISION IN PATIENTS WITH MACULAR DEGENERATION

(71) Applicant: SYNEOS HEALTH INTERNATIONAL LIMITED, Farnborough (GB)

(72) Inventors: Muhammad A. Qureshi, London (GB); Pablo Artal, Murcia (ES); Scott Robbie, London (GB)

(73) Assignee: SYNEOS HEALTH INTERNATIONAL LIMITED, Farnborough (GB)

( * ) Notice: Subject to any disclaimer, the term of this patent is extended or adjusted under 35 U.S.C. 154(b) by 37 days.

(21) Appl. No.: 17/479,437

(22) Filed: Sep. 20, 2021

(65) Prior Publication Data
US 2022/0000607 A1 Jan. 6, 2022

Related U.S. Application Data

(63) Continuation of application No. 16/691,590, filed on Nov. 21, 2019, now Pat. No. 11,147,662.

(60) Provisional application No. 62/770,999, filed on Nov. 23, 2018.

(51) Int. Cl.
A61F 2/16 (2006.01)

(52) U.S. Cl.
CPC .......... *A61F 2/1624* (2013.01); *A61F 2/1637* (2013.01)

(58) Field of Classification Search
CPC .......................... A61F 2/1624; A61F 2/1637
See application file for complete search history.

(56) References Cited

U.S. PATENT DOCUMENTS

| | | | |
|---|---|---|---|
| 2009/0204211 A1* | 8/2009 | Angelopoulos | A61F 2/1637 623/6.37 |
| 2009/0292354 A1 | 11/2009 | Gontijo et al. | |
| 2010/0318186 A1 | 12/2010 | Bumbalough et al. | |
| 2015/0250583 A1* | 9/2015 | Rosen | A61F 2/1613 623/6.11 |
| 2015/0320547 A1 | 11/2015 | Rosen et al. | |
| 2017/0258578 A1* | 9/2017 | Rosén | A61F 2/164 |
| 2018/0318065 A1 | 11/2018 | Rosen et al. | |

FOREIGN PATENT DOCUMENTS

| | | |
|---|---|---|
| EP | 2106770 A1 | 10/2009 |
| EP | 2591753 A1 | 5/2013 |
| WO | 2009142961 A1 | 11/2009 |
| WO | 2016142736 A1 | 9/2016 |

OTHER PUBLICATIONS

International Preliminary Report on Patentability in International Application No. PCT/IB2019/001255, dated May 25, 2021, pages.

(Continued)

*Primary Examiner* — Keri J Nelson
*Assistant Examiner* — Aren Patel
(74) *Attorney, Agent, or Firm* — DLA Piper LLP (US)

(57) ABSTRACT

An intraocular lens system comprising a single lens comprising two optical surfaces selected to maintain image quality at the foveal centre whilst reducing image aberration at preferred retinal locus locations outside of the fovea region.

5 Claims, 2 Drawing Sheets

(56) References Cited

OTHER PUBLICATIONS

PCT International Application No. PCT/IB2019/001255, International Search Report of The International Searching Authority, dated May 11, 2020, 4 pages.
PCT International Application No. PCT/IB2019/001255, Written Opinion of The International Searching Authority, dated May 11, 2020, 4 pages.

* cited by examiner

17 D      19 D      21 D      23 D      25 D

INTRA-OCULAR LENS FOR EXTENDED MACULAR VISION IN PATIENTS WITH MACULAR DEGENERATION

CROSS-REFERENCE TO RELATED APPLICATIONS

This non-provisional US utility patent application is a continuation of non-provisional U.S. utility patent application Ser. No. 16/691,590, filed 21 Nov. 2019, which claims the benefit of priority from U.S. provisional patent application No. 62/770,999, filed 23 Nov. 2018. The disclosure of such applications are herby incorporated by reference in their entireties where appropriate for teachings of additional or alternate details, features, and/or technical background, and priority is asserted from each.

BACKGROUND

In the decades since intraocular lenses (IOLs) were first introduced, the primary focus has been on optimising visual outcomes in normally-sighted individuals undergoing clear lens extraction and cataract surgery. This has led to the development of injectable soft acrylic IOLs, designed to minimise surgically-induced astigmatism, and aspherical lens optics to counter the age-related positive spherical aberration of the cornea. Standard soft acrylic intraocular lenses are now capable of delivering a tightly focused image at the fovea and consistent, high quality visual outcomes, in patients with otherwise healthy eyes. However, the quality of the image supplied by such lenses drops off significantly only a few degrees outside of the centre of the fovea and this may have significant implications for visual outcomes in patients with macular disease who often adopt eccentric fixation to make use of healthier retina outside of the foveal centre. Eyes with age-related macular degeneration have poor contrast sensitivity and scotomata (often centre-involving) that make them particularly sensitive to reductions in retinal image quality. Patients with center-involving macular disease can expect to have a degraded quality of vision with standard intraocular lenses that compounds the poor contrast sensitivity and patchy photoreceptor loss associated with conditions such as age-related macular degeneration (AMD). Furthermore, as conditions such as AMD progress, patients can expect the quality of the images supplied to preferred retinal loci to worsen as more of the macula becomes affected.

Surgical options for patients with macular pathology undergoing cataract extraction and intraocular lens implantation are extremely limited. To date, surgeons have largely used standard monofocal IOLs to target emmetropia and tightly focus the image at the foveal centre in such patients; however, the quality of the image supplied by standard IOLs drops off rapidly at only 4 degrees of retinal eccentricity (approximately 1.15 mm), despite cone density still being relatively high, at approximately 20000/mm$^2$, in this area[13].

Alternatives include the implantation of intraocular telescopes to provide a magnified image or the use of prismatic devices to target a single PRL. Some devices employ a combined approach. Patients with AMD frequently depend on the use of multiple preferred retinal loci to complete activities of daily living, so targeting a specific PRL has the disadvantage of compromising image quality at other retinal loci used for activities of daily living. Any image optimisation at a specific PRL may also become completely redundant if a patient starts to rely on another PRL as the disease progresses.

Intraocular telescopes attempt to build on the advantages of hand-held magnifiers by conferring the optical advantages of intraocular magnification and eliminating the need for hand-eye coordination. Such devices are often relatively large and complex when compared with standard IOLs and are more difficult to implant safely. A key drawback of intraocular telescopes, depending on the degree of magnification, is the reduction in peripheral visual field that results. With some devices, the peripheral field may be so constricted that implantation is only possible in one eye. Intraocular telescopes also disperse the finite amount of light across a wider area of retina, so inevitably reduce the contrast of the resulting image. Both intraocular telescopes and prismatic devices may therefore compromise patients' natural mechanisms for coping with central field loss and therefore impact on visual function because both contrast sensitivity and fixation stability correlate with reading ability. Similarly, reading function is likely to be disrupted if a device is only implanted in one eye by compromising binocular summation and affecting the scanning of the image across the macula that occurs during reading.

The evolution herein of a single, injectable, soft polymeric (e.g., acrylic) intraocular lens for implantation in the capsular bag, with optics uniquely configured to supply a focused image to all areas of the macula extending up to 10 degrees from the foveal centre is an advance on existing technologies. The optic is designed to maintain image quality at the centre of the fovea for patients with early disease. By correcting for optical aberrations generated when patients fixate eccentrically out to up to 10 degrees of retinal eccentricity, the embodiment IOL optimises visual potential in macular disease and protects against progressive visual loss. A target of +2D to +3.5D with such a novel intraocular lens may also afford 10-20% magnification with glasses but this is not essential to the mechanism of action.

BRIEF SUMMARY OF INVENTION

In an embodiment of the present invention, there is provided a single-piece, injectable, soft, hydrophobic polymeric (e.g., acrylic) intraocular lens designed for siting in the capsular bag. The lens optics are uniquely optimised to provide an enhanced quality of image anywhere in the macula from 0 degrees up to 10 degrees of eccentric fixation in any direction from the foveal centre. Embodiment lenses achieve their effect through being shaped to minimise the optical aberrations that would be generated by a standard lens if a patient were to fixate eccentrically. Embodiment lenses are designed to have radii and conic constants that provide for a focused image at the foveal center and a reduction in high order aberrations over an area extending up to, but not necessarily restricted to, 10 degrees from the focal center in all directions of gaze.

The novel lens delivers superior image quality compared with standard monofocal IOLs at increasing degrees of retinal eccentricity with potential benefits for patients with macular pathology. An embodiment IOL may be used to target a hypermetropic post-operative refraction: a target of +2D to +3.5D may afford 10-20% magnification with glasses. Emmetropia or myopic outcomes may be targeted in individuals with better visual potential or to avoid post-operative anisometropia, as with a standard monofocal IOL.

Embodiment IOL powers are available in dioptric powers of 11, 13, 15, 17, 19, 21, 23 and 25 D, but an embodiment IOL is not restricted to this range of dioptric powers. Suitable IOL power for an individual eye may be estimated using the SRK/T (or similar) biometric formula and an A-constant of 119.2, in a similar manner to standard IOLs implanted at the time of cataract surgery.

An embodiment IOL offers clear advantages over existing intraocular telescopes in the management of macular disease. By comparison, intraocular telescopes such as the Implantable Miniature Telescope (IMT) and the Intraocular Lens for Visually Impaired People (IOL-Vip™) are costly and complex devices, comparatively, that have risk-benefit profiles rendered less attractive by the need for large incisions in the eye, reductions in visual field, the risks of corneal decompensation and the need for post-operative visual rehabilitation[11,12]

In an embodiment, the invention is a single-piece, injectable, soft, hydrophobic polymeric (e.g., acrylic) IOL designed for sitting in the capsular bag. The lens optics are uniquely optimized to provide an enhanced quality of image across all areas of the macula extending 10° from the foveal center and the device therefore constitutes a new class of IOL.

As set forth in Example 1, the lens delivers superior image quality compared with standard monofocal IOLs at increasing degrees of retinal eccentricity with potential benefits for patients with macular pathology. The inventive IOL embodiment may also be used to target a hypermetropic postoperative refraction. For example, a target of +2.00 to +3.50 diopters affords 10% to 20% magnification with glasses, but the degree of hypermetropia may be increased or reduced depending on the severity of the maculopathy and the patient's preference or suitability for this approach. Emmetropia or myopic outcomes may be targeted in individuals with better visual potential or to avoid postoperative anisometropia, as with a standard monofocal IOL.

In embodiments there is provided an intraocular lens system for improving patient's vision enhancing the quality of image across all areas of the macular extending 10% from the foveal center comprising a lens having a first surface and a second surface, and providing an optical power of P diopters; the lens being characterized by an optical zone diameter (D) and a central thickness (T); the first surface is spherical having a first radius of curvature ($R_1$); the second surface is a rotationally symmetric conic surface, having a second radius of curvature ($R_2$), and having surface sag (z coordinate) which is a function of a radial coordinate (r) is given by:

$$z = \frac{cr^2}{1 + \sqrt{1 - (1+k)c^2 r^2}} \text{ where: } c = 1/R_2$$

$k$ = constant

In a specific embodiment, the preferred variables are P=11 diopters, D=6.00 mm, T=0.7 mm, $R_1$=19.99 mm, $R_2$=−143.7 mm, and k=−12.7. In another specific embodiment, the preferred variables are P=17 diopters, D=6.00 mm, T=0.7 mm, $R_1$=110.53 mm, $R_2$=−12.96 mm, and k=−12.7. In an additional specific embodiment, the preferred variables are P=25 diopters, D=6.00 mm, T=0.7 mm, $R_1$=−45.52 mm, $R_2$ is in the range from −6 mm to −19 mm, and k=−12.7.

DESCRIPTION OF DRAWINGS

Embodiments of the invention are illustrated in the accompanying drawings in which.

DETAILED DESCRIPTION

Standard monofocal IOLs provide a focused image to the fovea. In patients with dry AMD, central GA often results in a loss of functional vision at the fovea. However, there is still sufficient receptor density/visual function in the peripheral macula, to enable patients to maintain functional vision if the patient is able to fixate eccentrically.

The invention, as herein disclosed in embodiment IOLs, is designed to maintain image quality at the foveal centre but correct the optical aberrations that would be generated by a standard monofocal IOL when the eye is tilted to adopt eccentric fixation. This optimises image quality in any area within 10 degrees of the foveal centre thereby facilitating use of these areas as PRLs and resulting in improved functional outcomes after implantation. The objective is to provide good retinal images at up to 10 degrees of eccentricity with the option of mild magnification when combined with an external spectacle to correct for a maximum +3D refractive target.

Figure 1:
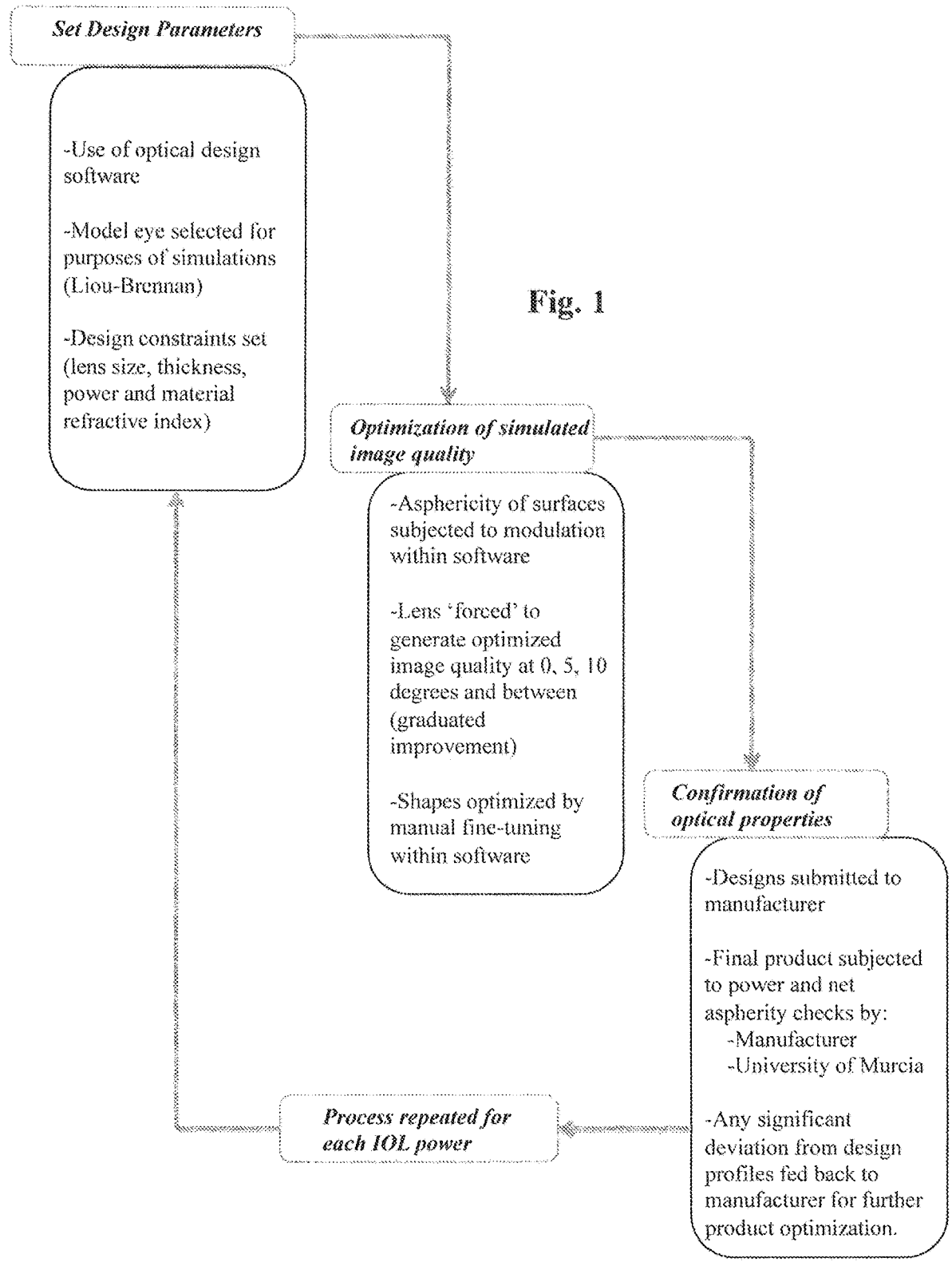
FIG. 1 is a schematic diagram of the design process.
Figure 2:
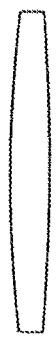
FIG. 2 is a profile view of an embodiment IOL, providing 17 diopter optical power.
Figure 3:
FIG. 3 is a profile view of an embodiment IOL providing 19 diopter optical power.
Figure 4:
FIG. 4 is a profile view of an embodiment IOL providing 21 diopter optical power.
Figure 5:
FIG. 5 is a profile view of an embodiment IOL, providing 23 diopter optical power.
Figure 6:
FIG. 6 is a profile view of an embodiment IOL providing 25 diopter optical power.

The embodiment IOL design may be carried out using commercially available ray-tracing software (Zemax OpticStudio, Zemax LLC, USA) in an eye model describing an average eye taken from the literature (Liou-Brenan: Liou H L, Brennan N A. Anatomically accurate, finite model eye for optical modelling. J Opt Soc Am A. 1997; 14(8)1684-1695.). FIG. 1 is a schematic diagram of an embodiment of the design process Ray-tracing techniques may be used to optimize the optical performance of different IOLs within the previously described eye model. An optical design software may be employed (Zemax OptieStudio, Zemax LLC, USA). Once the materials are selected, a merit function may be developed to design the embodiment IOLs. In general, the parameters may be selected across those of relevance for the intended performance of the lens. During the optimization procedure, different values may be systematically given to the independent variables. Subsequently, those may be employed to calculate the selected merit function components. The target is to find a set of values for the variables that minimize the merit function. In the ideal case, the procedure finishes with the finding of a global or absolute minimum, rather of a local minimum. The merit function generated incorporated constraints for the geometrical parameters of the IOL to keep them within physiologically compatible ranges. The variable parameters for the optimization, in this example, were the thickness of the lens, its position within the capsule, the radius of curvature, and the asphericity of the different surfaces. Three configurations were simultaneously included in the merit function corresponding to incoming beams on axis, at 5, and at 10 degrees of eccentricity in the horizontal direction.

Embodiment IOLs have the following features in common:

The front surface is a standard spherical surface with range or radius of curvature.

The rear surface is a rotationally symmetric conic surface. The surface sag (z coordinate) as a function of the radial coordinate r is given by:

$$z = \frac{cr^2}{1+\sqrt{1-(1+k)c^2r^2}}$$

where c is the inverse of the radius of curvature R: c=1/R

For a specific non-limiting 17D version of the lens, the relevant parameters are:

Optical zone diameter: 6.00 mm
Central thickness: 0.7 mm
1st (front) surface:
  Standard spherical surface
  Radius of curvature 110.53 mm
2nd (rear) surface:
  Rotationally symmetric conic surface. The surface sag (z coordinate) as a function of the radial coordinate r is given by:

$$z = \frac{cr^2}{1+\sqrt{1-(1+k)c^2r^2}}$$

for the anterior and posterior surfaces, respectively), refractive index of 1.54 and a thickness of 0.70 mm, was used.

To assess the embodiment IOLs' image quality the NIMO instrument (LAMBDA-X, Nivelles, Belgium) is used, which includes an optical bench, together with its software version 4.5.15. The working principle of this instrument is based on a phase-shifting schlieren techonology[71/72]. By combining the principle of schlieren imaging with the phase-shifting method, the NIMO instrument allows the measurement of light beam deviations, which can be used to calculate the wavefront analysis considering the 36 Zernikes coefficients. This technology has been shown to effectively measure in vitro optical quality of intraocular lenses. The apparatus complies with the International Standard Organization (ISO) 11979-216. All IOLs were measured while being immersed in a saline solution whose composition was 0.154 milliequivalents per milliliter of NaCl (Laboratories Sterop SA, Anderlecht, Belgium). The cuvettes or wet cells used to hold the IOLs and the saline solution in place during the measurements have been verified by means of an interferometer; and were shown to have a power <0.005 D. This additional cross-check on the wet cells was carried out to rule out potential interferences with the measurement. Moreover, accurate power measurements are only possible if the setup has been, thoroughly calibrated, which is why the instrument was calibrated for each measurement.

In Example 1 detailed below, the axial length of the eye model was set at 23.5 mm. Corneal parameters (curvature, asphericity, thickness and refractive index) were taken from the Liou-Brennan eye model (reference). The retina was simulated as a −12 mm sphere and the anterior IOL surface was placed axially at 4.16 mm from the second surface of the cornea.

The external spectacle lens was modelled using a refractive index of 1.585 (polycarbonate) and, a central thickness of 5 mm placed at 12 mm from the conical apex (vertex distance). Radii of curvature were 32 mm and 36 mm for the front and back surfaces respectively (1-3 dioptres). Additionally, a +6 D spectacle lens (with the object placed at 33 cm from the cornea), with the same front curvature but a posterior radius of curvature of 44.7 mm, was simulated. All calculations were performed at a wavelength of 550 mm and a pupil diameter of 3 mm.

The embodiment IOL lens was optimized for a Refractive Index of 1.54 (for 550 nm) and Abbe Number of 40 and for a thickness of 0.70 mm.

This optimization procedure was repeated for different models with defined axial length values. This provides optimized lenses for different powers. FIGS. 2 through 6 show the actual shape of the optimized embodiment IOLs of different powers. The corresponding emmetropic target is at the bottom of each lens. Using these methodology settings and targets, for this non-limiting example: as the dioptric power of the IOL increases, the posterior surface of the lens becomes more curved while the anterior surface changes the sign of the curvature, running from positive curvature to a flatter curvature and then negative curvature. This is the consequence of the shape factor optimization procedure for each model.

EXAMPLE 1

The Study

A study was designed and conducted to assess safety and initial outcomes following implantation of this novel intraocular lens in patients with advanced, bilateral age-related macular degeneration. Eight eyes of 7 subjects with ≤1+ cataract (no LOCSIII grading parameter >2), bilateral, advanced geographic atrophy/dry age-related macular degeneration (AMD) and preoperative corrected distance visual acuity ≥0.60 (CDVA; LogMAR), underwent lens extraction and IOL implantation with a hypermetropic postoperative refractive target. The amount of targeted postoperative hypermetropia was decided on after careful discussion with the patient regarding the potential benefits of magnification afforded with spectacles using this approach, balanced with the disadvantages of increased glasses dependence for activities of daily living. All patients had moderate-to-severe visual loss in the operated eye and so opted to have hypermetropic outcomes of 1.5D to 4.5D depending on individual circumstances (including agreement to proceed with surgery on the second eye if necessary). Initial follow-ups and assessments were undertaken at baseline, 1 week, 1 month and 2 months.

The following investigations were performed at baseline and 1 week, 1 month and 2 months post-operatively: full subjective refraction, corrected near visual acuity (N-point at 30 cm with LogMAR conversion), corrected distance visual acuity (LogMAR), intraocular pressure (Goldmann applanation tonometry), specular microscopy (Nidek CEM-530, Nidek Co, Ltd.; 3 acceptable images derived from the central cornea), clinical examination, anterior segment OCT (Visante, Carl Zeiss Meditec AG) and macular OCT (Stratus OCT™ Carl Zeiss Meditec, Germany). Lenticular opacities were graded according to the LOCSIII system. Visual fields were assessed by full-threshold 80-point testing. Reading acuity, critical print size and reading speed were assessed using the MNREAD chart after refractive error correction at 1 month post-operatively in the operated eye. Microperimetry was performed at baseline and at 1-2 months post-operatively using the Macular Integrity Assessment (MAIA, Ellex Medical Lasers Ltd.); additional microperimetric assessments were performed 1-3 months apart to confirm any changes observed. Microperimetry was undertaken under mesopic conditions with no mydriasis using the 'expert' algorithm to assess macular threshold sensitivity and fixation stability (37 points tested in a 10-degree area centred on the preferred retinal locus; 4-2 strategy; stimulus size Goldmann III with duration 200 ms). Exclusion criteria included: active choroidal neovascularisation (CNV) treated within 6 months of recruitment; axial length >24.5 mm or <20.5 mm; uncontrolled glaucoma and intraocular surgery within 6 months of recruitment.

The mean age of patients was 77+16 years (range 43-91) with a male-female ratio of 5:3. Surgery was performed by a single surgeon (MAQ) using standard techniques. Topical mydriatic agents were used for pupil dilation and anaesthesia was induced by sub-Tenon's delivery. A 5 mm capsulotomy and crystalline lens fragmentation were undertaken using a femtosecond laser surgery platform (LenSx®, Alcon®, Fort Worth, Tex., USA) and lens extraction completed using the WHITESTAR Signature® phacoemulsification system (Abbot Medical Optics, Abbot Laboratories Inc., Illinois, USA) with a standard 2.6 mm corneal incision sited at 100°. The capsular bag was filled with a cohesive ophthalmic viscoelastic device (OVD) and the lens then loaded into the injector cartridge, followed by injection into the capsular bag via the main wound, centration of the lens and OVD/balanced salt solution exchange. All subjects achieved a post-operative spherical equivalent within 1D of the targeted refraction (mean±2.9±1.3D).

Results

Specular microscopy revealed mean of reductions in endothelial cell counts post-operatively to be 13±14% (range 0-37%). 2 eyes had reductions of 37% and 31%—this subject was lost to follow-up after 2 weeks and lack of drop compliance may account for these changes. Results were otherwise in line with reductions expected following standard phacoemulsification cataract surgery (4-13%)[8]. 80-point visual field testing results were similar pre- and post-operatively (mean number of points seen was 50±31 pre-operatively compared with 53±27 post-operatively) and anterior segment and macular OCT imaging revealed well-centred IOLs and stable maculae post-operatively. Intraocular pressures remained stable in all subjects post-operatively—mean pre- and post-operative intraocular pressures were 16±2.8 mmHg and 14±2 mmHg, respectively at 2 months.

Post-operative MN read data were unavailable for one subject. In the remainder we observed modest improvements in mean reading acuity from 1.07±0.31 LogMAR to 0.9±0.37 LogMAR and in critical print size from 1.04±0.25 to 0.95±0.27. Mean reading speed was observed to increase from 28±19 words per minute to 44±31 words per minute, an improvement of 57%.

Microperimetry data were obtained at approximately 1 and/or 2 months post-operatively in all but one of the subject eyes. A mean improvement in microperimetry threshold sensitivities from 8.2±4.6 dB to 1.2.0±5.6 dB was observed. The mean percentage of fixation points within a 4-degree circle increased from 77±17% to 91±11%. Whilst post-operative microperimetry data were unavailable for one subject visual acuities improved significantly in this individual post-implantation. Minimal changes on microperimetric testing were observed in three eyes post-operatively with evidence of incremental improvements at 1 and 2 months in the remainder.

Further microperimetry testing for three of the operated eyes was undertaken and these data indicated incremental improvements in visual function beyond the 2-month timepoint. Preferred retinal loci in these eyes were observed to shift progressively away from areas of geographic atrophy. In subject eye 1, the average threshold sensitivity increased from 0 dB to 16.6 dB at 5 months with an associated increase in mean percentage of fixation points within a 4-degree circle from 64% to 94%. For this subject's second eye, testing at 4 months post-operatively indicated a slight reduction in average threshold sensitivity from 4.2 dB to 3 dB but an increase in the mean percentage of fixation points within a 4-degree circle from 57% to 93%, these points were concentrated in a narrow corridor between the optic disc and a large area of geographic atrophy. Testing in a third subject at 4 months showed an increase in threshold sensitivity from 112.9 dB to 27 dB and a slight decrease in mean percentage of fixation points within a 4-degree circle from 99% to 83%.

No symptoms of aniseikonia were reported but all subjects later went on to have their other eye implanted with the device.

Visual outcomes in study subjects with moderate-to-severe age-related macular degeneration that were consistent with the results of laboratory simulations, with the equivalent of a mean improvement in distance and near acuities of 18 ETDRS letters and a 57% increase in mean reading speed were observed. These results compare very favourably with published cataract surgery outcomes in AMD patients, including those undergoing treatment for CNV—recent meta-analysis indicated that subjects with AMD, undergoing cataract surgery and implantation with standard monofocal IOLs, can expect improvements in visual acuities of 6.5-7.5 ETDRS letters after 6-12 months of follow-up[9,10].

Statement Regarding Preferred Embodiments

While the invention has been described with respect to the forgoing, those skilled in the art will readily appreciate that various changes and/or modifications can be made to the invention without departing from the spirit or scope of the invention as defined by the appended claims.

The invention claimed is:
1. A method for manufacturing an intraocular lens (IOL) system for improving patient's vision, the method comprising:
forming a lens from a soft hydrophobic polymeric compound, the lens having a first surface and a second surface and an optical power of P diopters;
said lens being characterized by an optical zone diameter (D) and a central thickness (T);
said first surface is spherical having a first radius of curvature (R1);
said second surface is a rotationally symmetric conic surface, having a second radius of curvature (R2), and having surface sag (z coordinate) which is a function of a radial coordinate (r) is given by:

$$z = \frac{cr^2}{1 + \sqrt{1 - (1+k)c^2 r^2}}$$

where: c=1/r,
k=conic constant;
wherein as the dioptric power of the lens increases by more than one diopter, the conic constant remains constant.

2. The method of claim 1, wherein as the dioptric power of the lens increases, the posterior surface of the lens becomes more curved while the anterior surface changes the sign of the curvature, running from positive curvature to flatter and then negative curvature.

3. The method of claim 1, wherein:
P=11 diopters
D=6.00 mm
T=0.7 mm
R1=19.99 mm
R2=−143.7 mm
k=−12.7.

4. The method of claim 1, wherein:
P=17 diopters
D=6.00 mm
T=0.7 mm
R1=110.53 mm
R2=−12.96 mm
k=−12.7.

5. The method of claim 1, wherein:
P=25 diopters
D=6.00 mm
T=0.7 mm
R1=−45.52 mm
R2-6 to −19 mm
k==−12.7.

\* \* \* \* \*